(12) United States Patent
Boutet et al.

(10) Patent No.: US 8,906,268 B2
(45) Date of Patent: Dec. 9, 2014

(54) BIMODAL ORGAN PHANTOM AND ASSOCIATED PRODUCTION METHOD

(75) Inventors: Jérôme Boutet, Claix (FR); Didier Vray, Ternay (FR); Nadia Djaker, Marseilles (FR); Laurent Guyon, Grenoble (FR); Laurent Saroul, Grenoble (FR); Denis Friboulet, Lyons (FR); François Duboeuf, Villeurbanne (FR)

(73) Assignees: Commissariat a l'Energie Atomique et aux Energies Alternatives, Paris (FR); Centre National de Recherche Scientifique, Paris (FR)

( * ) Notice: Subject to any disclaimer, the term of this patent is extended or adjusted under 35 U.S.C. 154(b) by 59 days.

(21) Appl. No.: 13/497,040

(22) PCT Filed: Sep. 1, 2010

(86) PCT No.: PCT/EP2010/062809
§ 371 (c)(1),
(2), (4) Date: Apr. 10, 2012

(87) PCT Pub. No.: WO2011/032840
PCT Pub. Date: Mar. 24, 2011

(65) Prior Publication Data
US 2012/0193582 A1    Aug. 2, 2012

(30) Foreign Application Priority Data
Sep. 18, 2009  (FR) ...................................... 09 04476

(51) Int. Cl.
*G01N 31/00* (2006.01)
*A61B 5/055* (2006.01)
*A61B 8/08* (2006.01)
*A61B 8/00* (2006.01)
*A61B 5/00* (2006.01)
*G09B 23/28* (2006.01)

(52) U.S. Cl.
CPC ....... *A61B 5/0059* (2013.01); *A61B 2560/0233* (2013.01); *A61B 8/08* (2013.01); *A61B 8/587* (2013.01); *G09B 23/286* (2013.01)
USPC .......... 252/408.1; 424/9.3; 424/9.37; 436/15; 436/17

(58) Field of Classification Search
USPC .................................................... 252/408.1
See application file for complete search history.

(56) References Cited

U.S. PATENT DOCUMENTS

2012/0223051 A1*  9/2012  Millward ........................ 216/49

FOREIGN PATENT DOCUMENTS

WO        2009/045885 A2     4/2009

OTHER PUBLICATIONS

Chris L. Korte et al.: "Characterization of Plaque Components With Intravascular Ultrasound Elastography in Human Femoral and Coronary Arteries In Vitro," Circulation, Journal of the American Heart Association,102(6), pp. 617-623, 2000.

(Continued)

*Primary Examiner* — Jill Warden
*Assistant Examiner* — Brittany Fisher
(74) *Attorney, Agent, or Firm* — Baker & Hostetler LLP

(57) ABSTRACT

A phantom for medical imaging instrumentation, the phantom including a first hydrogel matrix, said matrix containing additives for simulating the optical and acoustic properties of a living organ or tissue. In the phantom, the additives include Indian ink or haemoglobin, silica powder and titanium dioxide powder. The phantom may contain a tumor simulator in solid or liquid form. It may also comprise several hydrogel matrices, each matrix including additives in different concentrations depending on the organ or tissue simulated. A method of producing the phantom includes one or more freeze-thaw cycles for optimizing the characteristics of the phantom.

17 Claims, 6 Drawing Sheets

(56) References Cited

OTHER PUBLICATIONS

Linda K. Ryan et al.: "Tissue Equivalent Vessel Phantoms for Intravascular Untrasound," Ultrasound in Medicine & Biology, vol. 23, No. 2, pp. 261-273, 1997.

Jeremy C. Hebden et al.: "A soft deformable tissue-equivalent phantom for diffuse optical tomography," Physics in Medicine and Biology, vol. 51, issue 21, pp. 5581-5590, 2006.

John Baeten et al.: "Develpoment of fluorescent materials for Diffuse Fluorescence Tomography standards and phantoms," Optics Express, vol. 15, No. 14, pp. 8681-8694, Jul. 9, 2007.

Mark McDonald et al.: "Multi-modality tissue-mimicking phantom for thermal therapy," Physics in Medicine & Biology, 49, pp. 2767-2778, 2004.

Tomas Svensson et al.: "In vivo optical characterization of human prostate tissue using near-infrared time-resolved spectroscopy," Journal of Biomedical Optics 12(1), 2007.

Ernest L. Madsen et al.: "Anthropomorphic Breast Phantoms for Qualification of Investigators for ACRIN Protocol 6666," Radiology, vol. 239, No. 3, pp. 869-874, Jun. 2006.

Jeremie Fromageau et al.: "Characterization of PVA Cryogel for Intravascular Ultrasound Elasticity Imaging," IEEE Transactions on Ultrasonics, Ferroelectrics, and Frequency Control, 50(10), pp. 1318-1324, 2003.

Johan M. Thijssen: "Ultrasonic speckle formation, analysis and processing applied to tissue characterization," Pattern Recognition Letters 24, pp. 659-675, 2003.

Olivier Bernard et al.: "Statistical Modeling of the Radio-Frequency Signal for Partially-and Fully-Developed Speckle Based on a Generalized Gaussian Model with Application to Echocardiography," IEEE Transactions on Untrasonics, Ferroelectrics, and Frequency Control, vol. 54, No. 10, pp. 2189-2194, Oct. 2007.

Yang Sun et al.: "Novel tissue phantom for testing a dual-modality diagnostic system: time-resolved fluorescence speactroscopy and high frequency ultrasound," SPIE, PO Box 10, Bellingham, WA 98227-0010, USA, vol. 6780, 2008.

Gloria M. Spirou et al.: "Note; Optical and acoustic properties at 1064 nm of polyvinyl chloride-plastisol for use as a tissue phantom in biomedical optoacoustics; Optical and acoustic properties of PVCP," Physics in Medicine and Biology, Taylor and Francis Ltd., London, GB, vol. 50, No. 14, Jul. 21, 2005, pp. N141-N153.

K. Zell et al.: "Note; Acoustical properties of selected tissue phantom materials for ultrasound imaging; Acoustical properties of selected phantom materials for optoacoustics," Physics in Medicine and Biology, Taylor and Francis Ltd., London, GB, vol. 52, No. 20, Oct. 21, 2007, pp. N475-N484.

C. Usha Devi et al.: "Design, fabrication, and characterization of a tissue-equivalent phantom for optical elastography," Journal of Biomedical Optics, vol. 10, No. 4, 2005.

Kim et al.: "Optical phantoms for ultrasound-modulated optical tomography," SPIE, PO Box 10, Bellingham, WA 98227-0010, USA, vol. 6870, 2008.

* cited by examiner

BIMODAL ORGAN PHANTOM AND ASSOCIATED PRODUCTION METHOD

CROSS-REFERENCE TO RELATED APPLICATIONS

This application is a National Stage of International patent application PCT/EP2010/062809, filed on Sep. 1, 2010, which claims priority to foreign French patent application No. FR 09 04476, filed on Sep. 18, 2009, the disclosures of each of which are incorporated by reference in their entireties.

FIELD OF THE DISCLOSED SUBJECT MATTER

The field of the invention is that of phantoms needed for calibrating and evaluating the performance of medical imaging instruments and the algorithms used for processing the images produced.

BACKGROUND

These phantoms are used to simulate the optical and/or acoustic properties of an organ and its environment. They also make it possible to simulate diseased organs containing, for example, tumors. They are manufactured in a reproducible and controlled manner.

However, most of the time these phantoms are dedicated to single-modality (monomodal) imaging, which may be optical or acoustic. However, recently, multi-modality (multimodal) imaging has experienced considerable growth in the medical diagnostic field. This is because it makes it possible to obtain both morphological and functional information. The morphological information is obtained by the use of x-rays or ultrasound. The functional information is obtained by using PET (positron emission tomography), MRI (magnetic resonance imaging) or fluorescence techniques. In particular, coupling ultrasonic imaging with fluorescence imaging seems to be particularly relevant for certain medical applications, such as mammography or diseases of the brain, prostate or testicles, since these two imaging techniques are compatible in terms of cost, size of the probes and depth of penetration. In this case, the phantom must enable both optical properties and acoustic properties to be simulated. The optical properties to be simulated are the light absorption ($\mu a$) and the light scattering ($\mu s'$) by the organ. The ultrasonic properties to be simulated are the power backscattered by the organ, which may be determined by measuring the average intensity of the signal coming from one or more sensors constituting an echographic probe. These ultrasonic parameters are also statistical parameters of the signal, such as the signal-noise ratio, or indicators determined by processing the acoustic signal such as, for example, the effective density of the scatterers present.

The literature describes phantoms for simulating the ultrasonic characteristics of living tissue. In particular, mention may be made of the following publications: de Korte, C. L., Pasterkamp, G., van der Steen, A. F. W., Woutman, H. A. and Born, N. (2000), "*Characterization of Plaque Components With Intravascular Ultrasound Elastography in Human Femoral and Coronary Arteries In Vitro*", Circulation 102(6), 617-623; Ryan, L. K. and Foster, F. S. (1997) "*Tissue equivalent vessel phantoms for intravascular ultrasound.*" Ultrasound in Medicine and Biology 23: 261-273 and also Madsen, E. L., Berg, W A., Mendelson, E. B. and Frank, G. R., "*Anthropomorphic breast phantoms for qualification of Investigators for ACRIN Protocol 6666*", Radiology, 2006 June, 239(3):869-74.

There are also publications on the simulation of optical characteristics, such as scattering and absorption. The following publications may be mentioned: Hebden, J. C., Price, B. D., Gibson, A. P., et al. "*A soft deformable tissue-equivalent phantom for diffuse optical tomography*", Physics in Medicine and Biology, Volume: 51 Issue: 21 Pages: 5581-5590 and Baeten, J., Niedre, M., Dunham, J., et al., "*Development of fluorescent materials for diffuse fluorescence tomography standards and phantoms*", Optics Express Volume: 15 Issue: 14 Pages: 8681-8694.

Also found are bimodal phantoms for other imaging modes. Thus, Bronskill's team describes, in the reference publication McDonald, M., Lochhead, S., Chopra, R. and Bronskill, M. J. (2004), "Multi-modality tissue-mimicking phantom for thermal therapy." Physics in Medicine and Biology 49: 2767-2778, a phantom mimicking the ultrasonic and optical properties of living tissue. However, this phantom represents only the light absorption characteristic and not the essential scattering characteristic.

SUMMARY

The phantom according to the invention makes it possible to simulate all the optical and acoustic properties of an organ that are necessary for bimodal medical imaging. It also makes it possible to simulate a diseased organ or the surrounding tissue. The method of obtaining it comprises a certain number of simple steps for obtaining a high-quality standard that remains constant over time. By varying the concentrations of the various components and the durations and parameters of the various steps or phases of the method, a large number of possible configurations may be simulated.

More precisely, one subject of the invention is a phantom for medical imaging instrumentation, comprising at least a first hydrogel matrix, said matrix containing additives for simulating the optical and acoustic properties of a living organ or tissue, characterized in that the additives are an absorbent liquid, silica powder and titanium dioxide powder.

Advantageously, the hydrogel consists of a mixture of water and PVA (polyvinyl alcohol); the volume concentration of PVA is between 5% and 20% of the volume of water; the absorbent liquid is Indian ink or haemoglobin; the volume concentration of the absorbent liquid is between 0% and 0.25% of the volume of water; the weight concentration of silica powder is between 0% and 4% of the weight of water and the weight concentration of titanium dioxide powder is between 0.0025% and 0.25% of the weight of water.

Advantageously, the phantom contains a tumor simulator in solid or in liquid form. In the latter case, said simulator may comprise at least one envelope containing the liquid, which liquid may be bovine haemoglobin or Indian ink, the concentration of which is greater than that of the absorbent liquid of the phantom, the envelope possibly being a polystyrene bead or a glass or Teflon (PTFE) capillary tube.

Advantageously, the phantom comprises several hydrogel matrices, each matrix containing additives for simulating the optical and acoustic properties of a different living organ or tissue so as to simulate an organ and its environment, the additives being Indian ink, silica powder and titanium dioxide powder in different concentrations depending on the simulated organ or tissue.

In one particular application, the simulated organ is a prostate gland.

Another subject of the invention is the method of producing said phantom, the latter comprising at least a first hydrogel matrix produced according to at least the following steps:

distilled water is poured into a container;
Indian ink is added to this distilled water;
PVA powder is added;
the above components are mixed together in a container of the beaker type with magnetic stirring, the mixture being thermostatically controlled;
silica powder is added during mixing;
titanium dioxide is added during mixing;
the mixture is heated and stirred;
the mixture is subjected to a vacuum; and
freeze-thaw cycles are carried out Advantageously, the number of freeze-thaw cycles is between 1 and 10, preferably between 2 and 6.

The matrices may be molded in nylon molds having the shape of the simulated organ.

BRIEF DESCRIPTION OF THE DRAWINGS

The invention will be better understood and other advantages will become apparent on reading the following description given by way of non-limiting example and by examining the appended figures in which.

DETAILED DESCRIPTION

Figure 1:
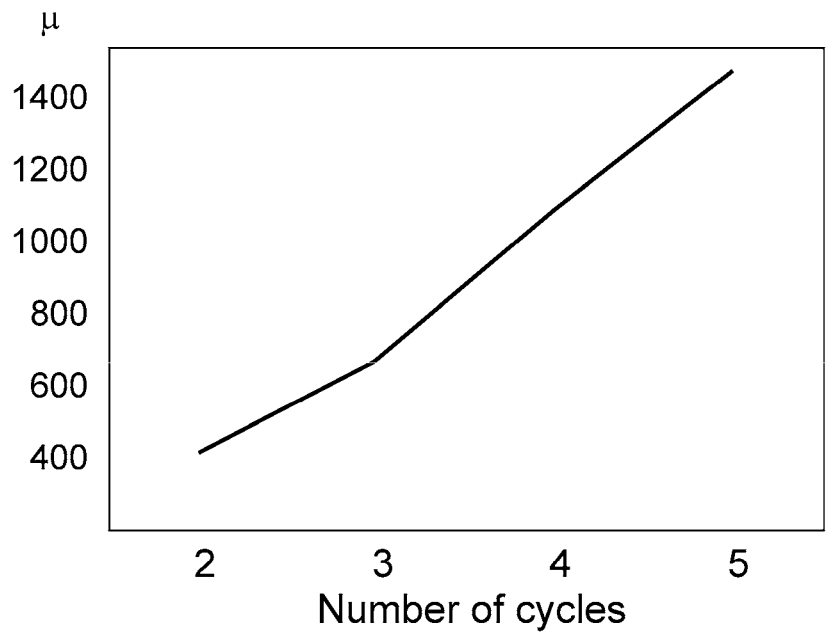
FIG. 1 shows the variation in the ultrasonic parameter μ (apparent integrated backscatter or AIB) as a function of the number of freeze cycles.

The objective of the invention is to produce a low-cost phantom for obtaining, within as wide a range as possible, the optical and ultrasonic properties of the organ that it is sought to simulate and as simply as possible. To be able to be easily exploited, this phantom must have a certain consistency and must not be degraded over time, thus avoiding any sedimentation effect.

The method of production according to the invention essentially consists in producing a hydrogel matrix into which additives are successively incorporated, which give said matrix ultrasonic and optical properties as close as possible to living tissue. Finally, the matrix undergoes physical treatments, such as a vacuum treatment and low-temperature cycles so as to perfect the characteristics of the phantom.

It is also possible to add one or more inclusions to this matrix that simulate one or more labeled tumours. The phantom may comprise several matrices, each matrix containing additives for simulating the optical and acoustic properties of a different living organ or tissue so as to simulate an organ and its complete environment.

The method of production according to the invention consists in producing a matrix filled with additives. Several types of hydrogel may be used. Notably, the following may be mentioned: agar-agar, a product extracted from certain algae; agarose gel, which is purified agar-agar; animal gelatin; or combinations of these components. The most appropriate is a PVA hydrogel, PVA having the advantage of being stable over a long time. It is largely insensitive to thermal, humidity and light variations. It is insensitive to photo-bleaching. Its optical refracted index of 1.36 is also close to that of human tissue, which varies between 1.33 and 1.55. By applying freeze/thaw cycles to the hydrogel, it goes from a viscous consistency to a firmer, more consistent and stronger state thus approaching the biological media to be simulated. Finally, additional molecules may be added without difficulty thereto during its preparation.

To give an example, for a PVA-based matrix having a volume of about 200 ml, the protocol for forming the matrix is the following:

in a first step, Indian ink and demineralized water are mixed together;

next, the PVA powder is diluted in the water-ink mixture. The molecular weight of the PVA may vary from 1000 g/mol to more than 100 000 g/mol. A molecular weight of 72 000 g/mol may be chosen;

after a first step of heating and mixing with a magnetic stirrer, the solution is then kept mixed so as to avoid any solid residue;

next, mixing continues for one hour thirty minutes at a temperature of approximately 80° C. with a heating magnetic stirrer, adding the various additives that will give the optical and ultrasonic properties. Once the mixture is homogeneous, it is poured into a solid mold and then degassed using a vacuum pump. The gel is then kept under a vacuum of about 510 mm of mercury for about 30 minutes; and finally, the gel is placed in a freezer programmed to carry out freeze-thaw cycles.

It should be noted that, to avoid difficulties associated with preparing greatly different volumes, mixtures corresponding to a given amount of distilled water may be systematically prepared, whatever the final volume of the simulated organ. This thus avoids having to adjust the amounts, the temperatures and the cycle times. Only the useful amount of gel is then kept.

The additives for simulating the optical properties are Indian ink and titanium oxide ($TiO_2$) powder. Adding ink to the distilled water serves to simulate light absorption characterized by the absorption coefficient pa. The $TiO_2$ particles serve to simulate optical scattering characterized by the reduced scattering coefficient μs'. The additives for simulating the ultrasonic properties are particles small enough in size in comparison with the wavelength of the emitted ultrasonic wave for simulating the acoustic scattering property. To give an example, silica ($SiO_2$) particles with a mean size of 10 microns are chosen. This compound has already been used previously in the production of ultrasonic phantoms. In this regard, the following publication may be mentioned: J. Fromageau, E. Brusseau, D. Vray, G. Gimenez and P. Delachartre, "*Characterization of PVA cryogel for intravascular ultra-* sound elasticity imaging", *IEEE Trans. Ultrasonic, Ferroelectric and Frequency Control*, 50(10):1318-1324, 2003.

The freeze-thaw cycles have an important effect on the optical properties of the matrix. To give an indication, a cycle lasting one day may comprise a freeze phase of about 10 hours at a temperature of −15° C. followed by a thaw phase of 14 hours at room temperature 20° C. Both the freezing and the thawing must be complete. Therefore, the freezing and thawing times must be adapted to the size of the gels. Preferably, the temperature is periodically checked during these cycles.

To summarize, in order to obtain the optical and ultrasonic properties of the simulated organ, it is possible to vary four parameters of the matrix, namely:

the number of freeze-thaw cycles;
the density of silica ($SiO_2$) particles, which mainly acts on the acoustic scattering;
the density of titanium oxide ($TiO_2$) particles which mainly acts on the optical scattering; and
the volume of Indian ink, which acts mainly on the optical absorption.

These parameters may be interdependent.

The optical properties of the phantom that are measured and have to have values close to the organ simulated by the phantom are the following:

$\mu s'$ (in $cm^{-1}$), namely the reduced scattering coefficient; and $\mu a$ (in $cm^{-1}$), namely the absorption coefficient.

These parameters vary with wavelength. It is usual to work with wavelengths lying in the red or near infra-red, in the 650 to 900 nanometer range.

The ultrasonic properties of the phantom that are measured and have to have values close to the organ simulated by the phantom are the following:

$\mu$, namely the apparent integrated backscatter (AIB) calculated from the average intensity of the scattered signal;
SNR, namely the signal/noise ratio;
$\alpha$, namely the effective density of scatterers.

It is very difficult to ensure reproducibility of the $\mu$ measurement between several echographs, as $\mu$ depends on the operating conditions, the probe used and post-treatments carried out. Thus, it is preferable to work in a relative manner on this parameter, hence the name "apparent" backscatter power. The parameter $\mu$ is a dimensionless quantity, namely the ratio of the measured average to the average of a reference phantom. Since a region of interest is examined, it is an "integrated" backscatter power. Thus, in the end, the parameter $\mu$ is called the apparent integrated backscatter or AIB.

In order to give an idea of the orders of magnitude of the optical and ultrasonic characteristics of human organs, the example of the prostate and its environment, comprising the rectal wall and surrounding tissue, may be taken. Among the articles in the literature, the paper by Svensson, T., et al., "*In vivo optical characterization of human prostate tissue using near-infrared time-resolved spectroscopy*". *Journal of Biomedical Optics*, 2007. 12(1) gives the optical characteristics of the prostate at red wavelengths.

As regards the ultrasonic properties, the three parameters measured on the prostate and described in the literature are very variable. However, representative ranges of these parameters may be determined.

To summarize, the values of the optical and ultrasonic parameters of the prostate and its environment are given in Table I below, the values in square brackets indicating the extreme values found:

TABLE I

| Parameter | Rectal wall | Prostate | Surrounding tissue |
|---|---|---|---|
| $\mu a$ ($cm^{-1}$) | 0.1 | 0.4 | 0.4 |
| $\mu s'$ ($cm^{-1}$) | 10 | 7 | 7 |
| $\mu$ | 3 $\mu(P)$ - [1.5-3 $\mu(P)$] | $\mu(P)$* | 3 $\mu(P)$ - [1.5-3 $\mu(P)$] |
| SNR | 1.4 - [1.3-1.7] | 1.5 - [1.3-1.7] | 1.4 - [1.3-1.7] |
| $\alpha$ | 1.5 - [1-4] | 2.5 - [1-4] | 1.5 - [1-4] |

*The prostate is the organ taken as reference for calibrating the rectal wall and the surrounding tissue.

These various optical and ultrasonic parameters are measured and monitored by means of monitoring equipment.

Figure 9:
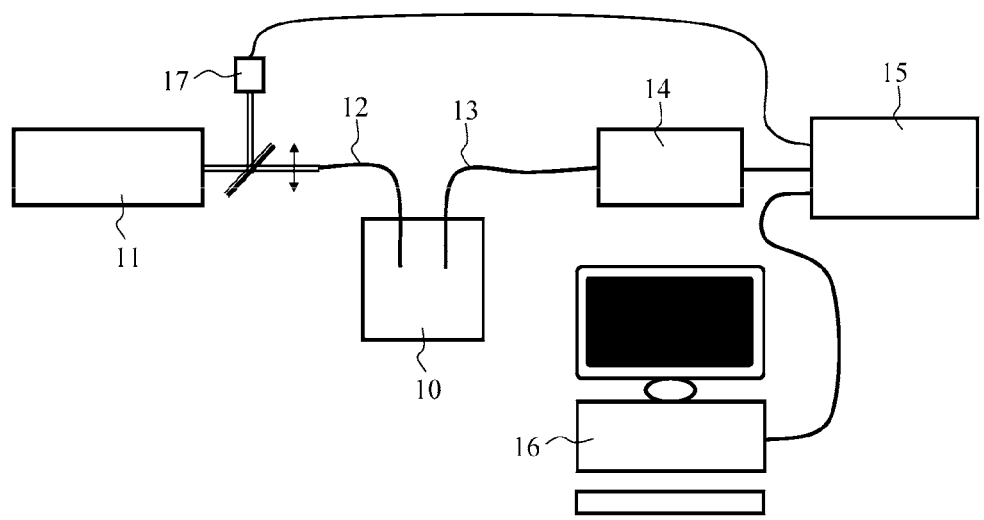
FIG. 9 shows a first set-up for characterizing the optical properties of the phantom by a photon counting system.

As a first example illustrated in FIG. 9, the equipment for optically characterizing a phantom 10 consists of a preferably wavelength-tunable pulsed laser source 11, optical transmission fibers 12 and 13 and a time-resolved detection system 14, 15. The light output by the source 11 is injected into the phantom 10 via a first, excitation fiber 12. After propagation and scattering in the phantom, the light is collected by a second, detection fiber 13 that sends the light to a time-resolved measurement device consisting of a photomultiplier 14 and a TCSPC (time-correlated single-photon counting) system 15 connected to a computer 16. A high-speed photodiode 17 takes off part of the pulsed optical system emitted by the source 11 and ensures synchronization with the counting system. The detection system makes it possible to obtain, after integration over a large number of emission pulses, reliable photon arrival time statistics. By comparing the experimental data with a model, these statistics may be used to obtain an approximate value of the absorption coefficient $\mu a$ and scattering coefficient $\mu s'$ of the object studied.

As a second example, the ultrasonic characterization is carried out by means of an echograph, comprising an ultrasonic probe that generates raw RF (radiofrequency) images. These raw images are acquired at the output of the probe before the transformations necessary for adjusting the display, such as the amplification or variable gain as a function of the depth. This data is used to calculate the envelope that will produce the resulting image, which is displayed on the screen of the echograph. To measure the characteristics of the medium, which are independent of the adjustments of the imaging system, it is necessary to analyze the RF image. By statistically analyzing the RF images and the envelope, it is possible to differentiate the various types of biological tissue, as demonstrated in the publication by J. M. Thijsen, "*Ultrasonic speckle formation, analysis and processing applied to tissue characterization*", *Pattern Recogn. Lett.* 24 (2003) 659-675. A K distribution model may be used to estimate the various parameters that account for the echogenicity, the local heterogeneity or the volume texture of tissue. "Echogenicity" is understood to mean the capability of organs to produce images of different tonality when ultrasonic waves pass through them. This model has the advantage of including the other ultrasonic statistical models, for example of the Rayleigh type. To give an example, the article by O. Bernard, B. Touil, J. D'hooge and D. Friboule, "*Statistical modeling of the radio-frequency signal for partially and fully developed speckle based on a generalized Gaussian model with application to echocardiography*", *IEEE Trans. Ultrason. Ferroelectr. and Freq. Control*, 54(10):2189-2194, 2007 gives information about this type of model.

To measure these parameters, the phantom is placed in water. The ultrasonic probe is placed above the phantom and several images are acquired after the probe has been moved transversely along the phantom. The signal is analyzed in a small region around the focal spot, which is placed at the center of the phantom.

The average and the standard deviation of these parameters are calculated over all the images acquired during the transverse scanning of the phantom, so as to improve and determine the measurement precision. It is preferable to carry out a large number of discrete acquisitions so as to obtain good measurement statistics.

FIGS. 1 to 8 show the variation in the various optical and ultrasonic parameters as a function of the four principal parameters of the matrix, these being the number of freeze-thaw cycles, the density of silica ($SiO_2$) particles, the density of titanium oxide ($TiO_2$) particles and the volume of absorbent liquid, in this case Indian ink. Of course, the ranges of each parameter are chosen so as to give optical and ultrasonic characteristics representative of the simulated organs.

Figure 2:
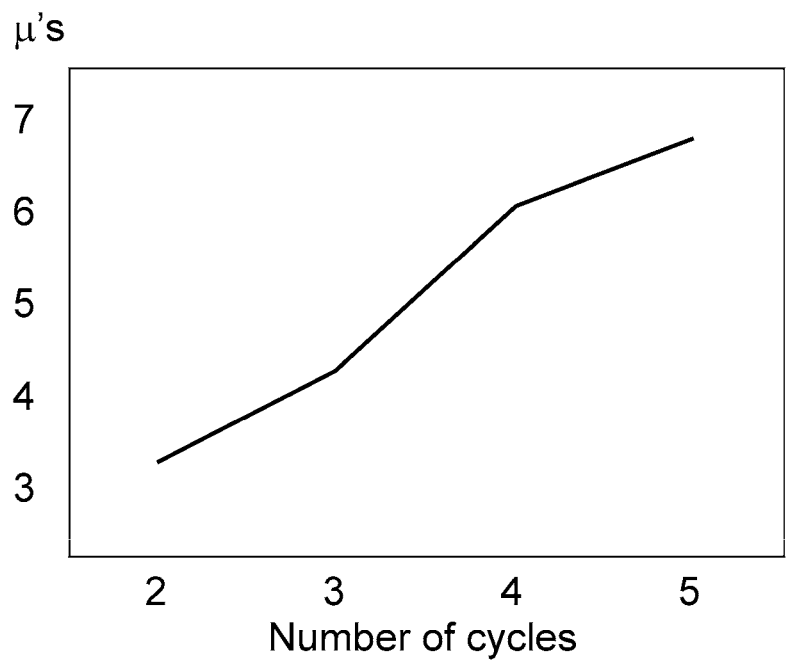
FIG. 2 shows the variation in the optical scattering coefficient μs' as a function of the number of freeze cycles.

FIGS. 1 and 2 show that the ultrasonic parameter $\mu$ or AIB and the optical parameter $\mu s'$ increase very significantly with the number of freeze-thaw cycles of a cryogel phantom containing no additive.

Figure 3:
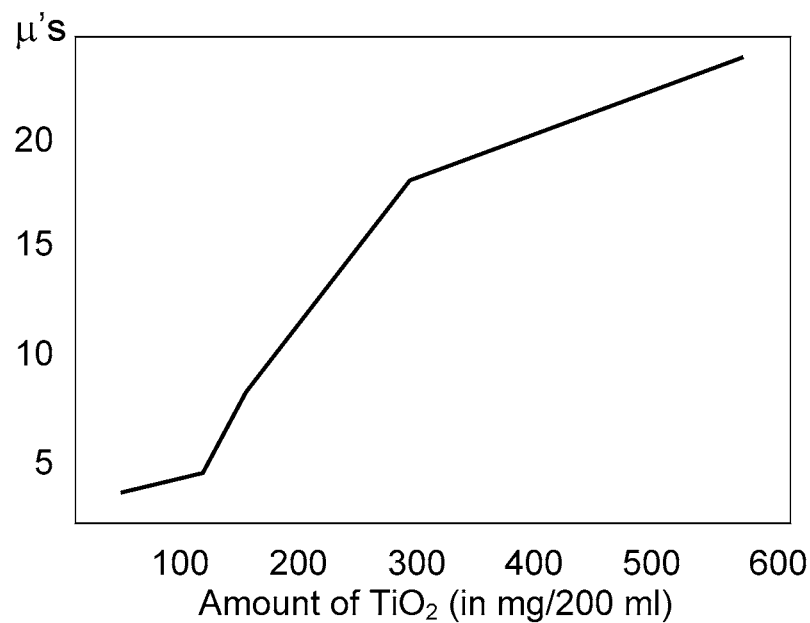
FIG. 3 shows the variation in the optical scattering coefficient μs' as a function of the amount of $TiO_2$.
Figure 4:
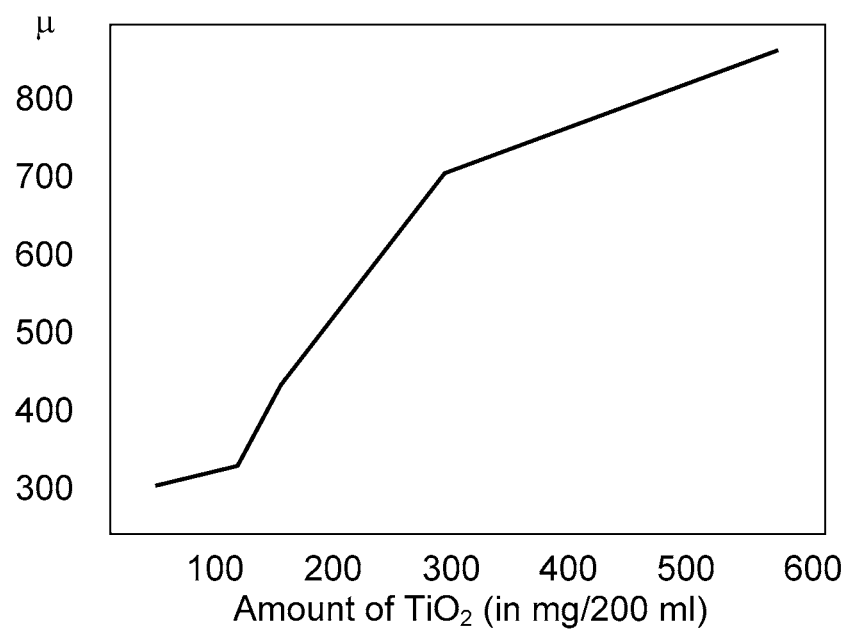
FIG. 4 shows the variation in the ultrasonic parameter μ (AIB) as a function of the amount of $TiO_2$.
Figure 5:
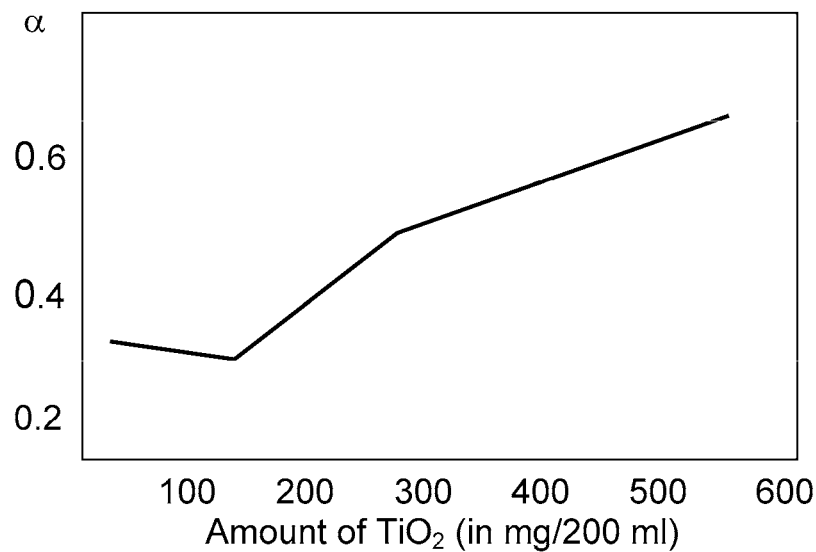
FIG. 5 shows the variation in the effective amount of scatterer α as a function of the amount of $TiO_2$.

FIGS. 3, 4 and 5 show that adding $TiO_2$ has an influence not only on the optical parameter $\mu s'$ (FIG. 3) but also on the ultrasonic parameters $\mu$ and $\alpha$ (FIGS. 4 and 5).

Figure 6:
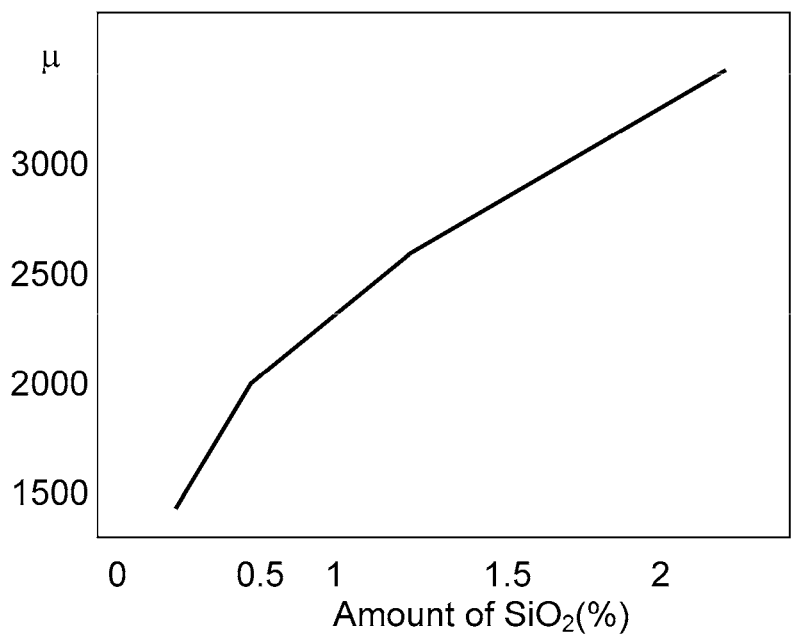
FIG. 6 shows the variation in the ultrasonic parameter μ (AIB) as a function of the amount of $SiO_2$ given as a percentage of the weight of distilled water.

FIG. 6 shows that the addition of $SiO_2$ has an influence on the ultrasonic parameter $\mu$.

Figure 7:
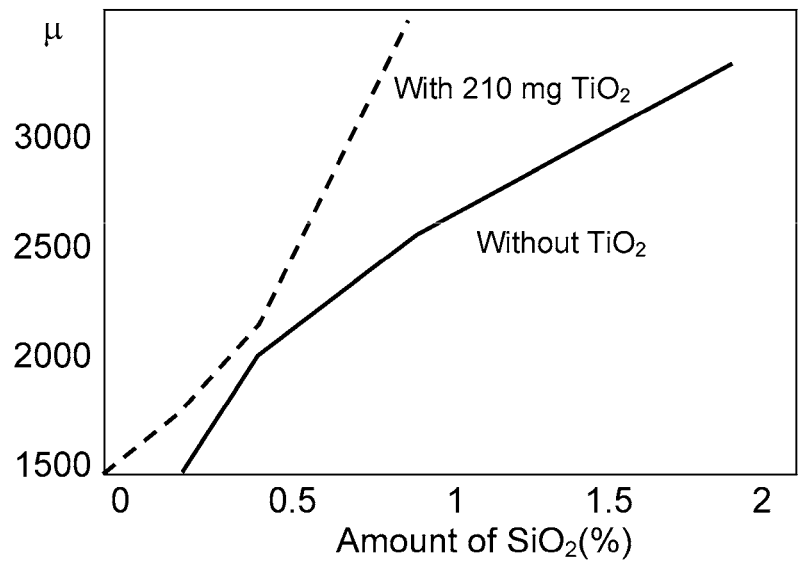
FIG. 7 shows the variation in the ultrasonic parameter μ (AIB) as a function of the amount of $SiO_2$, without $TiO_2$ and with $TiO_2$.

FIG. 7 shows that the addition of $SiO_2$ has an influence on the ultrasonic parameter $\mu$ and that this influence is different depending on whether or not the phantom contains $TiO_2$. Thus, the lower curve in this figure represents the variation in the ultrasonic parameter $\mu$ as a function of the amount of $SiO_2$, with no addition of $TiO_2$ powder—it is identical to the curve shown in FIG. 6. The upper curve represents the variation in the ultrasonic parameter $\mu$ as a function of the amount of $SiO_2$ with a set amount of $TiO_2$ present.

Figure 8:
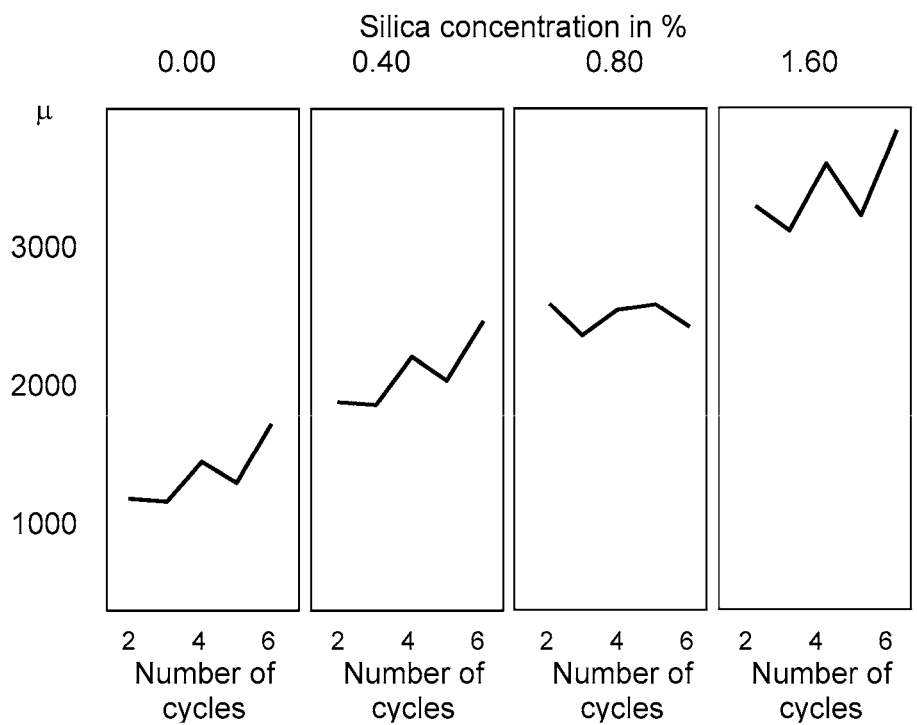
FIG. 8 shows the variation in the ultrasonic parameter μ (AIB) as a function of the freeze cycles and the amount of $SiO_2$ as a percentage of the weight of water.

Finally, FIG. 8 shows the mutual influence of the parameters, as may be seen in the set of curves, when $SiO_2$, $TiO_2$ and ink are present. These curves are plotted as a function of the number of freeze-thaw cycles, varying between 1 and 6. In the first curve on the left, the $SiO_2$ and $TiO_2$ concentrations are zero. For the other three curves, the amount of $TiO_2$ is fixed at 80 mg/200 ml of water and the amount of ink at 40 μl/200 ml, the amount of $SiO_2$ varying from 0.4 to 1.6%. These curves make it possible to choose the values of the parameters for fixing the desired properties of the phantoms. It should be noted that with the addition of $SiO_2$ and/or $TiO_2$, the number of freeze-thaw cycles has very little influence on the ultrasonic and optical parameters, whereas without $SiO_2$ and/or $TiO_2$, the freeze cycles have a major influence.

These measurements show that it is possible, by varying the various parameters, to simulate all of the optical and ultrasonic properties of organs very appropriately. They also show that there is interdependence between the four main parameters of the matrix.

To summarize, in order to produce a phantom representative of an organ, the parameters must lie within the following ranges:
  number of cycles: between 1 and 10, preferably between 2 and 6;
  PVA concentration: between 5 and 20%, preferably 10%;
  $TiO_2$ content: between 5 and 500 mg/200 ml, preferably between 5 and 200 mg/200 ml;
  silica content: between 0 and 4%, preferably between 0.2 and 2%;
  amount of ink: between 1 and 500 μl/200 ml, preferably between 1 and 100 μl/200 ml.

An alternative to using Indian ink is to use haemoglobin, for example bovine haemoglobin. In this case, the concentration is similar to the Indian ink concentration specified above.

Figure 11:
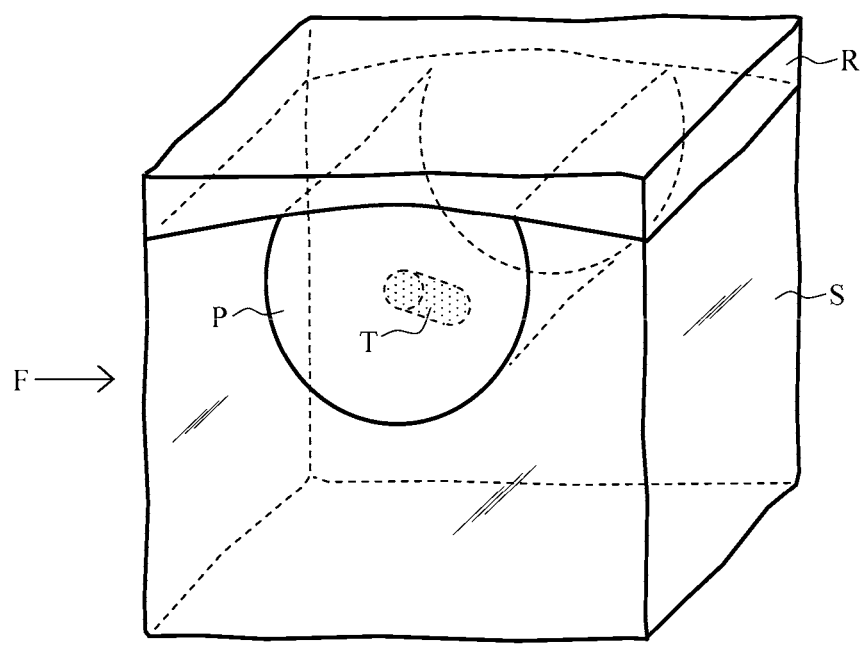
FIG. 11 shows a perspective view of a prostate phantom and its environment according to the invention.

To give a non-limiting example, an optical-ultrasonic bimodal phantom F according to the invention simulating a prostate and its environment is shown in FIG. 11. It has the shape of a rectangular parallelepiped, 6 centimeters in length and 5 centimeters in height and depth, i.e. a volume of about 150 ml. As may be seen in FIG. 11, the phantom comprises three parts, simulating the rectal epithelium R, the surrounding connective tissue S and the prostate gland tissue P taking the form of a truncated cylinder.

The material used to produce the phantom was a cryogel, the common name for a polyvinyl alcohol (PVA) gel.

The concentrations of the additives necessary for simulating the optical and ultrasonic properties of the prostrate and its surroundings are given in Table II below:

TABLE II

| Parameter | Rectal wall | Prostate | Surrounding tissue |
|---|---|---|---|
| Number of cycles | 4 | 2 | 3 |
| $TiO_2$ content (mg/200 ml) | 160 | 80 | 40 |
| Silica content (%) | 1.6% | 0.4% | 1.6% |
| Ink (μl/200 ml) | ≤10 | 40 | 40 |

As Table II shows, to be able to produce, in sequence, the various parts and best adapt the characteristics of the modeled parts to the corresponding tissue, the various layers did not undergo the same number of freeze-thaw cycles. Thus the matrix simulating the prostate underwent two cycles, the matrix simulating the tissue three cycles and the matrix simulating the rectal wall four cycles.

The optical and ultrasonic properties of the prostate phantom obtained from these various parameters are given in Table III below:

TABLE III

| Parameter | Rectal wall | Prostate | Surrounding tissue |
|---|---|---|---|
| $\mu a$ (cm$^{-1}$) | Not applicable | 0.45 ± 0.1 | 0.5 ± 0.1 |
| $\mu s'$ (cm$^{-1}$) | Not applicable | 5.4 ± 1 | 4.8 ± 1 |
| $\mu$ | 1.88 μ(P) | μ(P)* | 1.72 μ(P) |
| SNR | 1.64 | 1.33 | 1.63 |
| $\alpha$ | 3.51 | 1.21 | 3.37 |

*The prostate is the organ taken as reference for calibrating the rectal wall and the surrounding tissue.

When the various values in Tables I and III are compared, it may be seen that the phantom has characteristics very close to the actual organ.

To produce this phantom, a nylon mold was used so as to minimize adhesion of the gel to the walls. The mold was made up of three interlocking parts necessary for casting and freezing the three layers in succession. The main portion of the mold has the form of a rectangular parallelepiped 6 centimeters in length and 5 centimeters in height and depth. The second portion has the form of a thin parallelepipedal block PB, comprising five flat faces and one curved face. The latter serves to give the part R a curved shape. Finally, the third portion is a truncated nylon cylinder TC, truncated at two thirds of its diameter over its entire height so as to form the location for the part P.

In a first step, the matrix simulating the rectal wall was produced. A first gel with its additives corresponding to the tissue R was poured into the second portion PB of the mold. This first matrix was placed in a freezer so as to undergo a freeze-thaw cycle.

In a second step, the portion PB was carefully removed, and the gel layer thus formed left in place. The cylindrical portion TC was placed in the mold against the first gel layer.

The second gel, corresponding to the tissue S, was then poured into the space thus formed. The assembly was then placed in a freezer so as to undergo a second freeze-thaw cycle.

In a third step, the portion TC was carefully removed. The location formed by removing the portion TC was filled with the gel corresponding to the tissue P. The assembly was then placed in a freezer so as to undergo two successive freeze-thaw cycles.

At this point in the production, R therefore underwent 4 cycles, S underwent 3 cycles and P underwent 2 cycles.

In the foregoing, the aim was to simulate healthy organs. It is of great interest to be able also to simulate diseased organs, that is to say those containing tumours. Tumours have a higher optical absorption coefficient than a healthy organ, owing to their high degree of vascularization. There are many possible ways of simulating an absorbent tumor. For example, the following may be used:

- an ink concentration greater than that of the phantom; and
- bovine haemoglobin: the advantage of this substance is that the wavelength dependence of the absorption by tissue can be simulated, but its drawback is that the lifetime of the phantom is reduced.

These liquids may be encapsulated in:

- polystyrene beads having a fixed diameter, typically of one millimeter;
- glass or Teflon capillary tubes.

These liquids may also be injected into the phantom, for example using a syringe.

A tumor may also be simulated by a solid, for example a fluorescent polymer or glass.

It is also possible to inject a concentration of ink directly into the phantom, using a syringe. In this way, a pocket of liquid more absorbent than the surrounding tissue is created locally.

In an example, it is possible to add a fluorescent inclusion T, represented by a cylinder in FIG. 11, to the phantom F described above, so as to simulate the presence of a labeled tumor. This fluorescent inclusion may also be absorbent for applications in which the NIR (near-infrared reflection) technique is used for the detection, i.e. a technique based solely on the contrast caused by the different absorption coefficient between healthy tissue and cancerous tissue.

In general, tumours are revealed both by fluorescence imaging and ultrasonic imaging. The objective is to locate the potentially cancerous zones and thus significantly reduce the number of biopsies necessary for a safe diagnosis. Ultrasound provides morphological information, such as the contours of the prostate, while fluorescence provides functional information, such as the presence or absence of tumours. In this case, the technique used consists, before the biopsy, in injecting a fluorescent carrier that concentrates specifically in the cancerous zones of the prostate. The depthwise search for the fluorescent zone is performed using a fiber-based time-resolved fluorescence tomography system within the endorectal probe intended for the ultrasound measurement.

Figure 10:
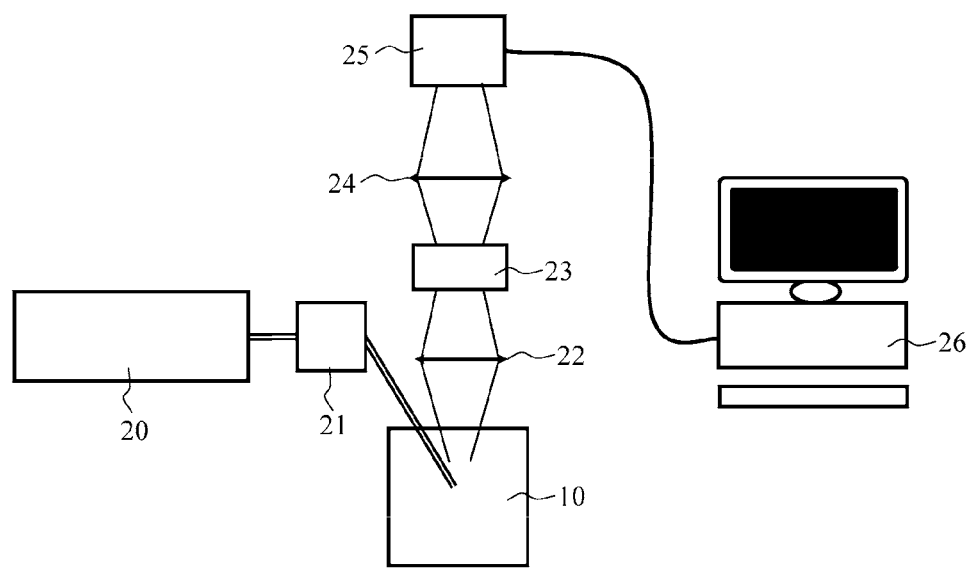
FIG. 10 shows a second set-up for characterizing the optical properties of the phantom by a fluorescence tomography system.

The phantoms according to the invention allow these techniques to be perfectly simulated using both fluorescence imaging and ultrasound imaging. The device shown in FIG. 10 is used. A pulsed laser 20 scans, using a deflection system 21, a phantom 10 comprising one or more inclusions simulating fluorescence-labeled tumours. The scan is performed in a predefined pattern. At each position of the laser, a series of time-resolved images is acquired by a light-intensifier/camera, comprising a first lens 22, an MCP (microchannel plate) light intensifier 23, a second lens 24 and a matrix photodetector 25 connected to a microcomputer 26. This camera integrates the light signal only over a very short time interval, of the order of 300 picoseconds, it being possible for the signal delay to be varied over a wide range, of the order of several nanoseconds. The stack of images produced makes it possible for the fluorescent inclusion to be located in three dimensions, after reconstruction using an algorithm based on the zero-order moments that give the average intensity of the signal and the first-order moments that are representative of the photon time of flight. It should be noted that for some applications, for example for prostate examination, the light from the laser source to the phantom and then from the phantom to the detector is generally transmitted via optical fibers.

These phantoms may thus be used for the purpose of calibrating an ultrasonic/optical bimodal instrument. For example, implanting thereinto three inclusions, that are both fluorescent and echogenic, it is possible to calibrate the two imaging modalities one with respect to the other. It is thus possible to determine the mathematical (translational, rotational and homothetic) transformations necessary for best combining the 3D maps obtained by the optical (fluorescence absorption) and ultrasound measurements.

These phantoms may be produced for simulating various organs and their environment: not only prostates, but also, non-limitingly, testicles, breasts, brains, etc.

To summarize, the advantages of the invention are the following:

- better calibration quality: by using a single phantom operating for two imaging modalities, it is thus possible to calibrate the two images one with respect to the other. In this way it is easy to make the origin and the direction of the axes of the reference frames coincide or to take account of the distortion between the images acquired with each of the modalities. This makes it possible to superimpose, later or else in real time, the functional images provided by the fluorescence technique on the morphological images provided by the ultrasound technique;
- a low cost: it is then possible to produce several sets of phantoms with diverse characteristics and geometries depending on the intended applications;
- greater measurement accuracy: a simultaneous ultrasound/ fluorescence measurement on a bimodal phantom gives more accurate results than two measurements on two separate phantoms. This is because, over the period when switching from one phantom to the other, several measurement biases may appear such as, for example, a change in the ambient conditions (temperature, relative humidity);
- greater operating simplicity, notably for the end users;
- space saving, when a single phantom is used instead of two phantoms; and
- relatively long storage time, exceeding several months.

The invention claimed is:

1. A phantom for medical imaging instrumentation, comprising a first hydrogel matrix, said matrix containing additives for simulating the optical and acoustic properties of a living organ or tissue, wherein the additives comprise at least one absorbent liquid, a silica powder and a titanium dioxide powder, the absorbent liquid including an absorber, said absorber being an ink or haemoglobin.

2. The phantom according to claim 1, wherein the hydrogel consists of a mixture of water and PVA (polyvinyl alcohol) powder, the volume concentration of the PVA is between 5% and 20% of the volume of the water.

3. The phantom according to claim 1, wherein the absorbent liquid is Indian ink.

4. The phantom according to claim 3, wherein the volume concentration of the Indian ink is between 0% and 0.25% of the volume of the water.

5. The phantom according to claim 1, wherein the weight concentration of the silica powder is between 0% and 4% of the weight of the water.

6. The phantom according to claim 1, wherein the weight concentration of the titanium dioxide powder is between 0.0025% and 0.25% of the weight of the water.

7. The phantom according to claim 1, further comprising a tumor simulator (T) in solid form.

8. The phantom according to claim 1, further comprising a tumor simulator (T) in liquid form.

9. The phantom according to claim 8, further comprising at least one envelope containing the liquid.

10. The phantom according to claim 8, wherein the liquid is bovine haemoglobin or Indian ink, the concentration of which is greater than that of the bovine haemoglobin or of the Indian ink of the phantom.

11. The phantom according to claim 9, wherein the envelope is a polystyrene bead or a glass or Teflon (PTFE) capillary tube.

12. The phantom according to claim 1, further comprising several hydrogel matrices, each matrix containing additives for simulating the optical and acoustic properties of a different living organ or tissue so as to simulate an organ and its environment, the additives comprising one absorbent liquid, a silica powder and a titanium dioxide powder in different concentrations depending on the simulated organ or tissue.

13. The phantom according to claim 12, wherein the simulated organ is a prostate gland.

14. A method of producing a phantom according to claim 2, the phantom comprising at least a first hydrogel matrix produced according to at least the following steps:
- distilled water is poured into a container;
- Indian ink is added to this distilled water;
- PVA powder is added;
- the distilled water, Indian ink and PVA powder are mixed together in a container of a beaker type with magnetic stirring, the mixture being thermostatically controlled;
- silica powder is added during mixing;
- titanium dioxide is added during mixing;
- the mixture is heated and stirred;
- the mixture is subjected to a vacuum; and
- one or more freeze-thaw cycles are carried out.

15. The method of producing a phantom according to claim 14, wherein the number of freeze-thaw cycles is between 1 and 10.

16. The method of producing a phantom according to claim 15, wherein the matrices are molded in nylon molds having the shape of the simulated organ.

17. The method of producing a phantom according to claim 14, wherein the number of freeze-thaw cycles is between 2 and 6.

* * * * *